United States Patent [19]

Kutsuki et al.

[11] Patent Number: 4,857,468
[45] Date of Patent: Aug. 15, 1989

[54] PROCESS FOR PREPARING OPTICALLY ACTIVE 2-HALO-1-PHENYL ETHANOL

[75] Inventors: Hidetoshi Kutsuki, Kobe; Ikuo Sawa; Natsuki Mori, both of Takasago; Junzo Hasegawa; Kiyoshi Watanabe, both of Akashi, all of Japan

[73] Assignee: Kanegafuchi Kagaku Kogyo Kabushiki Kaisha, Osaka, Japan

[21] Appl. No.: 849,985

[22] Filed: Apr. 10, 1986

[30] Foreign Application Priority Data

Apr. 13, 1985 [JP] Japan .................................. 60-79114
Apr. 13, 1985 [JP] Japan .................................. 60-79115
Sep. 14, 1985 [JP] Japan .................................. 60-203643
Sep. 14, 1985 [JP] Japan .................................. 60-203644

[51] Int. Cl.$^4$ ............................................. C07P 41/00
[52] U.S. Cl. ..................... 435/280; 435/156; 435/161; 435/171; 435/911; 435/921; 435/933; 435/940
[58] Field of Search ............... 435/280, 132, 136, 170, 435/171, 262

[56] References Cited

U.S. PATENT DOCUMENTS 3,076,750  2/1963  Muys et al. ................... 435/136
4,396,715  8/1983  Labows, Jr. et al. ........... 435/126

OTHER PUBLICATIONS

Chemical Abstracts, vol. 95. No. 7, p. 521, No. 113491m, Sep. 1981.
Chemical Abstracts, vol. 107, No. 7, p. 603, No. 54741m, Aug. 17, 1987.
J. Org. Chem. 45, 3352, (1980).
Tetrahedron Letters 22, 2527, (1981).
J. Chem. Soc., Chem. Comm., 1975, 400, (1975).

Primary Examiner—Robert J. Warden
Assistant Examiner—Janelle Graeter
Attorney, Agent, or Firm—Armstrong, Nikaido, Marmelstein, Kubovcik & Murray

[57] ABSTRACT

A process for preparing optically active 2-halo-1-phenyl ethanol having the general formula [I*]:

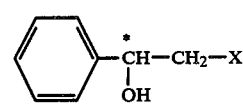

wherein X is a halogen atom, by asymmetrically reducing 2-halo-acetophenone having the general formula [II]:

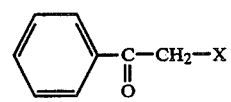

wherein X is as above, to give optically active 2-halo-1-phenyl ethanol, (R)-form or (S)-form, employing the microorganism.

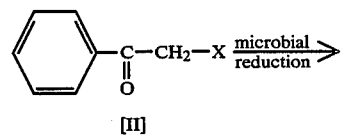

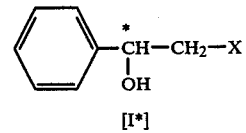

According to the present invention, optically active 2-halo-1-phenyl ethanol can be prepared with a good optical purity and yield in a simple process.

4 Claims, No Drawings

PROCESS FOR PREPARING OPTICALLY ACTIVE 2-HALO-1-PHENYL ETHANOL

BACKGROUND OF THE INVENTION

The present invention relates to a process for preparing optically active 2-halo-1-phenyl ethanol having the general formula [I*]:

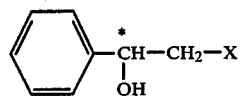

wherein X is a halogen atom, by asymmetrically reducing 2-halo-acetophenone having the general formula [III]:

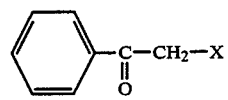

wherein X is as above, to give optically active 2-halo-1-phenyl ethanol, (R)-form or (S)-form, employing the microorganism.

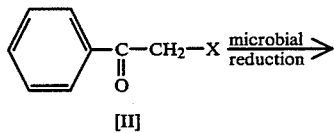

Since optically active 2-halo-1-phenyl ethanol has two highly reactive functional groups and can also be easily converted into optically active styrene oxide which has a high reactivity, it is a very useful starting material for synthesizing various drugs, veterinary drugs, agricultural chemicals, perfumes and the like.

Hitherto, several methods have been reported for preparing optically active 2-halo-1-phenyl ethanol by employing the enzyme or the microorganism. One of these methods is to asymmetrically reduce 2-chloro-acetophenone by employing *Saccharomyces cerevisiae* to give (R)-2-chloro-1-phenyl ethanol (D. D. Ridley et al., J. Chem. Soc. Chem. Comm., 400 (1975)). The other method is to asymmetrically reduce 2-chloro-acetophenone or 2-bromoacetophenone by employing *Cryptococcus macerans* to give (R)-2-chloro-1-phenyl ethanol or (R)-2-bromo-1-phenyl ethanol (M. Imuta et al., J. Org. Chem., 45, 3352 (1980)). However, these methods using the above microorganisms give (R)-2-chloro-1-phenyl ethanol with low optical activities, i.e. about 85% enantiomer excess (e.e.), as calculated by the present inventors, and with low productivities. Therefore, it is obvious that these methods are not suited for the industrial production. Further, these methods product only (R)-form but not (S)-form.

Another method is to subject an ester of (+)-2-halo-1-phenyl ethanol with fatty acid to the action of *Rhizopus nigricans* to give (R)-2-halo-1-phenyl ethanol (M. Imuta et al., Tetrahedron Lett., 22, 2527 (1981)). Also according to this method, only very low optical purity is obtained.

By the result of the continuous effort of the present inventors in order to establish a process for preparing both enantiomers of 2-halo-1-phenyl ethanol with a good optical purity and yield by asymmetrically reducing 2-halo-acetophenone by employing the various microorganisms, the inventors have found the microorganisms capable of converting 2-halo-acetophenone into (S)-2-halo-1-phenyl ethanol and the microorganisms which can convert 2-halo-acetophenone into (R)-2-halo-1-phenyl ethanol with an excellent optical purity.

SUMMARY OF THE INVENTION

According to the present invention, there is provided a process for preparing optically active (S)-2-halo-1-phenyl ethanol having the general formula [(S)-I]:

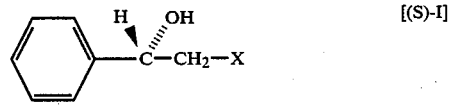

wherein X is a halogen atom, which comprises subjecting 2-halo-acetophenone having the general formula [II]:

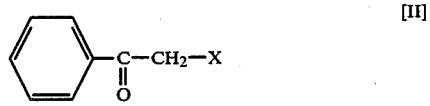

wherein X is as above, to the action of a microorganism of the genus selected from the group consisting of Candida, Debaryomyces, Saccharomyces, Saccharomycopsis, Torulopsis, Trichosporon, Sporidiobolus, Endomyces, Geotrichum, Nadsonia, Aegerita, Agrocybe, Arachnothica, Arxiella, Aspergillus, Beauveria, Botrytis, Chloridium, Cryptophiale, Cylindrocladium, Flammulina, Fusarium, Gibberella, Gilocladium, Gliomastix, Gymnoascus, Mortierella, Mucor, Paecilomyces, Penicillium, Scolecobasidium, Septoria and Stachybotrys which has an activity capable of asymmetrically reducing 2-halo-acetophenone [II] to give (S)-2-halo-1-phenyl ethanol [(S)-I], and isolating the obtained (S)-2-halo-1phenyl ethanol [(S)-I]. In the above general formulas [(S)-I] and [II], a halogen atom may be either Cl or Br. Examples of the microorganism which can be employed in the present invention are, for instance, *Candida humicola, Candida rugosa, Debaryomyces hansenii, Saccharomyces rouxii, Saccharomycopsis lipolytica, Torulopsis gropengiesseri, Trichosporon fermentans, Sporidiobolus johnsonii, Endomyces reessii, Geotrichum candidum, Nadsonia elongata, Aegerita candida, Agrocybe cyclyndracea, Arachnothica glomerata, Arxiella terrestris, Aspergillus niger, Beauveria bassiana, Botrytis fabae, Cloridium chlamydosporis, Cryptophiale guadalcanalense, Cylindrocladium camelliae, Flammulina veltipes, Fusarium culmorum, Gibberella fujikuroi, Gliocladium deliquescens, Gliomastix murorum, Gymnoascus reessii, Mortierella ramanniana, Mucor abundans, Paecilomyces elegans, Penicillium restrictum, Scolecobasidium terreum, Septoria triticic* and *Stachybotrys chartarum.*

Also according to the present invention, there is provided a process for preparing (R)-2-halo-1-phenyl ethanol having the general formula [(R)-I]:

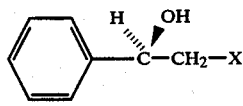 [(R)-I]

wherein X is a halogen atom, which comprises subjecting 2-halo-acetophenone having the general formula [II]:

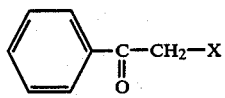 [II]

wherein X is as above, to the action of a microorganism of the genus selected from the group consisting of Hansenula, Candida, Rhodotorula, Torulopsis, Hanseniaspora, Filobasidium, Hormoascus and Kloeckera which has an activity capable of asymmetrically reducing 2-halo-acetophenone [II] to give (R)-2-halo-1-phenyl ethanol [(R)-I], and isolating the obtained (R)-2-halo-1-phenyl ethanol [(R)-I]. In the above general formulas [(R)-I] and [II], a halogen atom may be either Cl or Br. Examples of the microorganism which can be employed in the present invention are, for instance, *Hansenula anomala, Candida sake, Candida humicola, Rhodotorula glutinis, Rhodotorula glutinis var dairensis, Torulopsis pinus, Hanseniaspora valbyensis, Filobasidium capsuligenus, Hormoascus platyodis, Kloeckera africana* and the like.

According to the present invention, (S)-2-halo-1-phenyl ethanol with a high optical purity can be prepared with a good yield due to a discovery of the microorganism which can asymmetrically reduce 2-halo-acetophenone to give (S)-2-halo-1-phenyl ethanol. Also according to the present invention, (R)-2-halo-1-phenyl ethanol with a higher optical purity can be prepared than that prepared by the usual method.

DETAILED DESCRIPTION OF THE INVENTION

The microorganism, which can asymmetrically reduce 2-halo-acetophenone to give (S)- or (R)-2-halo-1-phenyl ethanol, employed in the present invention can be screened by the following method: i.e. 300 ml of a culture medium (medium A) having a composition of, for instance, 40 g of glucose, 3 g of yeast extract, 13 g of $(NH_4)_2HPO_4$, 7 g of $KH_2PO_4$, 0.8 g of $MgSO_4.7H_2O$, 60 mg of $ZnSO_4.7H_2O$, 90 mg of $FeSO_4.7H_2O$, 5 mg of $CuSO_4.5H_2O$, 10 mg of $MnSO_4.4H_2O$ and 0.1 g of NaCl in 1000 ml of water (pH 7.2) is put into a 2 l flask and, after sterilization, the microorganism is inoculated thereto, followed by a shaking culture at 30° C. for 2 days.

The cells are collected by centrifugation and are suspended in 75 ml of water containing 0.5% of 2-chloro-acetophenone and 5% of sucrose, the resultant being shaked in a 2 l flask at 30° C. for 2 to 3 days, to which an equivalent amount of ethyl acetate is added to extract the product, followed by a measurement of 2-chloro-1-phenyl ethanol by a gas chromatography (column: silicon OV-17, inner diameter: 1.3 cm, length: 200 cm, column temperature: 135° C., $N_2$ gas: 1.2 kg/cm²). On the other hand, the analysis of the optical purity of 2-chloro-1-phenyl ethanol is carried out by a high performance liquid chromatography (HPLC) (column: Chiralcel-OC, eluent: n-hexane-ethylether (30:1), flow rate: 2.2 ml/min, detection: 220 nm) after purifying the extraction product by distillation. Under these conditions, retention times for (R)-form and for (S)-form are 29 minutes and 33 minutes respectively and from these peak areas, optical purities of (R)-form and of (S)-form can be calculated.

The microorganism, which can convert 2-chloroacetophenone into (R)-2-chloro-1-phenyl ethanol, can also convert 2-bromo-acetophenone into (R)-2-bromo-1-phenyl ethanol while the microorgaism, which can convert 2-chloro-acetophenone into (S)-2-chloro-1-phenyl ethanol, can also convert 2-bromo-acetophenone into (S)-2-bromo-1-phenyl ethanol.

Examples of the microorganism employed for producing (S)-2-halo-1-phenyl ethanol from 2-halo-acetophenone are, for instance, *Candida humicula* CBS 2744, *Candida rugosa* IFO 0591, *Debaryomyces hansenii* IPO 0855, *Saccharomyces rouxii* IFO 0493, *Saccaromycopsis lipolytica* IFO 1209, *Torulopsis gropengiesseri* IFO 0659, *Trichosporon fermentans* IFO 1199, *Sporidobolus johnsonii* IFO 6903, *Endomyces reessii* CBS 179.60, *Geotrichum candidum* CBS 187.67, *Nadsonia elongata* IFO 0665, *Aegerita candida* IFO 6988, *Agrocybe cylyndracea* IFO 30299, *Arachnothica glomerata* IFO 9639, *Arxiella terrestris* IFO 30203, *Aspergillus niger* IFO 4280, *Beauveria bassiana* IFO 8554, *Botrytis fabae* IFO 5895, *Chloridium chlamydosporis* IFO 7070, *Cryptophiale quadalcanalense* IFO 30029, *Cylindrocladium camelliae* IFO 8979, *Flammulina veltipes* IFO 8329, *Fusarium culmorum* IFO 5902, *Gibberella fujikuroi* IFO 6604, *Gliocaldium deliquescens* IFO 6617, *Gliomastix murorum* IFO 8269, *Gymnoascus reessii* IFO 7639, *Mortierella ramanniana* IFO 7825, *Mucor abundans* IFO 9398, *Paecilomyces elegans* IFO 7060, *Penicillium restrictum* IFO 7922, *Scolecobasidium terreum* IFO 8854, *Septoria tritici* IFO 7347, *Stachybotrys chartarum* IFO 5369, and the like. Examples of the microorganism employed for producing (R)-2-halo-1-phenyl ethanol from 2-halo-acetophenon are, for instance, *Hansenula anomala* IFO 0120, *Hansenula anomala* IFO 0146, *Candida sake* CBS 2220, *Candida humicola* CBS 2754, *Candida humicola* CBS 1896, *Rhodotorula glutinis* IFO 1099, *Rhodotorula glutinis var dairensis* IFO 0415, *Torulopsis pinus* IFO 0741, *Hanseniaspora valbyensis* IFO 1758, *Filobasidium capsuligenus* IFO 1119, *Hormoascus platyodis* IFO 1471, *Kloeckera africana* IFO 0869, and the like.

(IFO: Institute of Fermentation, Osaka; Juso Nishinomachi, Higashi-yodogawa-ku, Osaka, Japan, CBS: Centraalbureau voor Schimmelcultures, yeast Division, Julianalean 67 A, Delft, The Netherlands)

For culturing the above microorganisms, any nutrient source which these microorganisms can usually assimilate can be employed. For example, there can be used the usual culture medium containing a carbon source carbohydrate source such as glucose or sucrose, an alcohol such as ethanol or glycerol, or a hydrocarbon such as paraffin, an organic acid such as acetic acid or propionic acid, or soybean oil or a mixture thereof a nitrogen-containing inorganic or organic source such as yeast extract, peptone, meat extract, corn steep liquor, ammonium sulfate, urea or ammonia, inorganic nutrient such as phosphate, magnesium, iron, manganese or potassium, and a vitamin such as biotin or thiamine in a proper amount. The culture is carried out at a pH of from 4.0 to 9.5 of the culture medium under an aerobic condition at a temperature ranging from 20° to 40° C. for 1 to 5 days.

The reduction is carried out by employing the culture broth as such, or by suspending the cells separated by centrifugation into a phosphate buffer, water and the like, to which 2-halo-acetophenone is added. In the reaction, carbon source such as glucose or sucrose may be added to the reaction mixture as an energy source. The cells may be alive or treated with acetone, lypholized, immobilized on a support and the like.

2-Halo-acetophenone may be added as such in a crystalline form or as a solution in an organic solvent or oil which does not disturb the reaction, all at once in the earliest stage of the reaction or in portions in the course of the reaction. The reaction is carried out at a temperature ranging from 10° to 60° C. at a pH of from 5 to 9 for 3 to 120 hours. Separation of optically active 2-halo-1-phenyl ethanol produced in the reaction is carried out by extraction from the reaction mixture as such or from a supernatant obtained after separation of the cells, with a solvent such as ethyl acetate or dichloromethane, the solvent layer being dehydrated, followed by distillation to give optically active 2-halo-1-phenyl ethanol with a high purity.

The present invention is more particularly described and explained by the following Examples. However, it should be understood that the present invention is not limited to the Examples and various changes and modifications can be made without departing from the scope and spirit of the present invention.

EXAMPLE 1

A 2 l flask was charged with 300 ml of the above-mentioned culture medium A. After sterilization, each microorganism of Table 1 was inoculated in the culture medium. A shaking culture was conducted under an aerobic condition at 30° C. for 2 days. The cells were collected by centrifugation of the culture broth. The obtained cells were suspended into 75 ml of 0.1M phosphate buffer (pH 7.0) containing 0.5% of 2-chloroacetophenone and 5% of sucrose and the resultant was put in a 2 l flask to conduct the reaction at 30° C. for 48 hours. After completion of the reaction, (S)-2-chloro-1-phenyl ethanol was extracted twice with ethyl acetate in an equivalent amount to the reaction mixture. (S)-2-Chloro-1-phenyl ethanol in the ethyl acetate layer was analyzed with a gas chromatography to calculate the yield. Ethyl acetate was removed under reduced pressure to given an oil, which was then purified by distillation to give (S)-2-chloro-1-phenyl ethanol with a high purity. An optical purity of the obtained (S)-2-chloro-1-phenyl ethanol was examined by an HPLC analysis. The results are shown in Table 1.

TABLE 1

| Microorganism | (S)-2-Chloro-1-phenyl ethanol | |
|---|---|---|
| | Yield (%) | Optical purity (% e.e.) |
| Candida humicola CBS 2774 | 100 | 100 |
| Candida rugosa IFO 0591 | 61 | 60 |
| Debaryomyces hansenii IFO 0855 | 46 | 100 |
| Saccharomyces rouxii IFO 0493 | 30 | 100 |
| Saccharomycopsis lipolytica IFO 1209 | 33 | 100 |
| Torulopsis gropengiesseri IFO 0659 | 79 | 88 |
| Trichosporon fermentans IFO 1199 | 55 | 61 |
| Sporidobolus johnsonii IFO 6903 | 98 | 25 |

TABLE 1-continued

| Microorganism | (S)-2-Chloro-1-phenyl ethanol | |
|---|---|---|
| | Yield (%) | Optical purity (% e.e.) |
| Endomyces reessii CBS 179.60 | 50 | 79 |
| Geotrichum candidum CBS 187.67 | 52 | 89 |
| Nadsonia elongata IFO 0665 | 66 | 61 |
| Aegerita candida IFO 6988 | 48 | 77 |
| Agrocybe cyclyndracea IFO 30299 | 26 | 79 |
| Arachnothica glomerata IFO 9639 | 38 | 88 |
| Arxiella terrestris IFO 3023 | 40 | 60 |
| Aspergillus niger IFO 4280 | 36 | 90 |
| Beauveria bassiana IFO 8554 | 46 | 78 |
| Botrytis fabae IFO 5895 | 30 | 77 |
| Chloridium chlamydosporis IFO 7070 | 60 | 67 |
| Cryptophiale guadalcanalense IFO 30029 | 26 | 81 |
| Cylindrocladium camelliae IFO 8979 | 47 | 74 |
| Flammulina veltipes IFO 8329 | 48 | 83 |
| Fusarium culmorum IFO 5902 | 32 | 88 |
| Gibberella fujikuroi IFO 6604 | 48 | 76 |
| Gliocladium deliquescens IFO 6617 | 24 | 87 |
| Gliomastix murorum IFO 8269 | 55 | 84 |
| Gymnoascus reessii IFO 7639 | 42 | 90 |
| Mortierella ramanniana IFO 7825 | 100 | 76 |
| Mucor abundans IFO 9398 | 96 | 77 |
| Paecilomyces elegans IFO 7060 | 55 | 80 |
| Penicillium restrictum IFO 7922 | 44 | 84 |
| Scolecobasidium terreum IFO 8854 | 28 | 70 |
| Septoria tritici IFO 7347 | 20 | 86 |
| Stachybotrys chartarum IFO 5369 | 26 | 80 |

EXAMPLE 2

The microorganisms as shown in Table 2 were cultured as in Example 1 and the cells were suspended in 0.1M phosphate buffer (pH 7.0) containing 0.5% of 2-bromo-acetophenone and 5% of sucrose. The reaction, extraction and analysis were carried out as in Example 1. The results are shown in Table 2.

TABLE 2

| Microorganism | (S)-2-Bromo-1-phenyl ethanol | |
|---|---|---|
| | Yield (%) | Optical purity (% e.e.) |
| Candida humicola CBS 2774 | 98 | 97 |
| Debaryomyces hansenii IFO 0855 | 52 | 100 |
| Saccharomyces rouxii IFO 0493 | 29 | 100 |
| Saccharomycopsis lipolytica IFO 1209 | 31 | 100 |
| Torulopsis gropengiesseri IFO 0659 | 68 | 87 |
| Endomyces reessii CBS 179.60 | 47 | 81 |
| Geotrichum candidum CBS 187.67 | 55 | 96 |

EXAMPLE 3

Candida humicola CBS 2774 was inoculated in 3 l of the culture medium A in a 5 l jar fermentor and the microorganism was cultured at 1 volume of gas per volume of liquid per minute of aeration at 30° C. at 500 rpm for 24 hours. After completion of the culture, cells were collected by centrifugation and suspended into 750 ml of water. Thereto 7.5 g of 2-chloro-acetophenone and 38 g of sucrose were added. With keeping the pH of the reaction mixture at 7.0 with NaOH, the reaction was carried out at 30° C. at 150 rpm for 24 hours. After completion of the reaction, (S)-2-chloro-1-phenyl ethanol was extracted with ethyl acetate from the reaction mixture. The ethyl acetate layer was dehydrated with anhydrous $Na_2SO_4$ and the solvent was removed under reduced pressure to give 8.5 g of oil, followed by distillation (75° to 76° C./2 mmHg) to give 5.8 g of colorless oil of (S)-2-chloro-1-phenyl ethanol.

The product had a specific rotatory power $[\alpha]_D^{25} +48.5°$ (C=2, cyclohexane) and an optical purity of 98% enantiomer excess by an HPLC analysis.

EXAMPLE 4

The procedure as in Example 3 was repeated except that 7.5 g of 2-bromo-acetophenone was employed as a substrate in place of 7.5 g of 2-chloro-acetophenone to give 4.2 g of (S)-2-bromo-1-phenyl ethanol (b.p. 85° C./0.5 mmHg). The product had a specific rotatory power $[\alpha]_D^{25} +48.7°$ (C=1, chloroform) and an optical purity of 97% enantiomer excess by an HPLC analysis.

EXAMPLE 5

The procedure as in Example 1 was repeated employing the microorganisms as shown in Table 3 to give (R)-2-chloro-1-phenyl ethanol. The optical purity was measured by an HPLC analysis as shown in Table 3.

TABLE 3

| Microorganism | (R)-2-Chloro-1-phenyl ethanol | |
|---|---|---|
| | Yield (%) | Optical purity (% e.e.) |
| Hansenula anomala IFO 0120 | 64 | 100 |
| Hansenula anomala IFO 0146 | 62 | 100 |
| Candida sake CBS 2220 | 43 | 47 |
| Candida humicola CBS 2756 | 49 | 100 |
| Candida humicola CBS 1896 | 100 | 99 |
| Rhodotorula glutinis IFO 1099 | 66 | 100 |
| Rhodotorula glutinis var dairensis IFO 0415 | 99 | 100 |
| Torulopsis pinus IFO 0741 | 100 | 100 |
| Hanseniaspora valbyensis IFO 1758 | 22 | 100 |
| Filobasidium capsuligenus IFO 1119 | 26 | 100 |
| Hormoascus platyodis IFO 1471 | 26 | 100 |
| Kloeckera africana IFO 0869 | 29 | 100 |

EXAMPLE 6

The procedure as in Example 1 was repeated except that the microorganisms as shown in Table 4 were employed and the cells were suspended in 75 ml of 0.1M phosphate buffer (pH 7.0) containing 0.5% of 2-bromo-acetophenone and 5% of sucrose. The results are shown in Table 4.

TABLE 4

| Microorganism | (R)-2-Bromo-1-phenyl ethanol | |
|---|---|---|
| | Yield (%) | Optical purity (% e.e.) |
| Hansenula anomala IFO 0120 | 58 | 100 |
| Hansenula anomala IFO 0146 | 60 | 100 |
| Candida humicola CBS 2756 | 30 | 100 |
| Rhodotorula glutinis IFO 1099 | 70 | 100 |
| Rhodotorula glutinis var dairensis IFO 0415 | 98 | 100 |
| Torulopsis pinus IFO 0741 | 80 | 100 |
| Hanseniaspora valbyensis IFO 1758 | 17 | 100 |
| Filobasidium capsuligenus IFO 1119 | 23 | 100 |
| Hormoascus platyodis IFO 1471 | 21 | 100 |
| Kloeckera africana IFO 0869 | 25 | 100 |

EXAMPLE 7

The procedure as in Example 3 was repeated except \t Rhodotorula glutinis IFO 1099 in place of Candida nicola CBS 2774 was employed to give 6.2 g of (R)- loro-1-phenyl ethanol. The product had a specific rotatory power $[\alpha]_D^{25} -51.1°$ (C=1, cyclohexane) and an optical purity of 100% enantiomer excess by an HPLC analysis.

EXAMPLE 8

The procedure as in Example 3 was repeated except that Rhodotorula glutinis IFO 1099 in place of Candida humicola CBS 2774 and 7.5 g of 2-bromo-acetophenone in place of 2-chloro-acetophenone were employed to give 6.7 g of (R)-2-bromo-1-phenyl ethanol. The product had a specific rotatory power $[\alpha]_D^{25} -49.2°$ (C=1, chloroform) and an optical purity of 100% enantiomer excess by an HPLC analysis.

What we claim is:

1. A process for preparing optically active (S)-2-halo-1-phenyl ethanol having the general formula [(S)-I]:

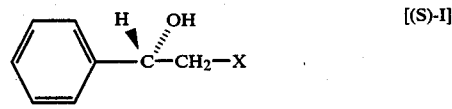

wherein X is a halogen atom, which comprises subjecting 2-halo-acetophenone having the formula [II]:

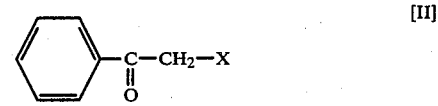

wherein X is as above, to the action of a microorganism selected from the group consisting of Candida humicola CBS 2774, Candida rugosa IFO 0591, Debaryomyces hansenii IFO 0855, Saccharomyces rouxii IFO 0493, Saccaromycopsis lipolytica IFO 1209, Torulopsis gropenglesseri IFO 0659, Trichosporon fermentans IFO 1199, Sporidobolus johnsonni IFO 6903, Endomyces reessii, CBS 179.60, Geotrichum candidum CBS 187.67, Nadsonia elongata IFO 0665, Aegerita candida IFO 6988, Agrocybe cylyndracea IFO 30299, Arachnothica glomerata IFO 9639, Arxiella terretris IFO 30203, Aspergillus niger IFO 4280, Beauveria bassiana IFO 8554, Botrytis fabas IFO 5895, Chloridium chlamydosporis IFO 7070, Cryptophiale guadalcanalense IFO 30029, Cylindrocladium camelliae IFO 8979, Flammulina veltipes IFO 8329, Fusarium culmorum IFO 5902, Gibberella fujikuroi IFO 6604, Gliocladium deliquescens IFO 6617, Gliomastix murorum IFO 8269, Gymnoascus reessii IFO 7639, Mortierella ramanniana IFO 7825, Mucor abundans IFO 9398, Paecilomyces elegans IFO 7060, Penicillium restrictum IFO 7922, Scolecobasidium terreum IFO 8854, Septoria tritici IFO 7347 and Stachybotrys chartarum IFO 5369.

2. The process of claim 1, wherein X is Cl or Br in formulas [(S)-I] and [II].

3. A process for preparing (R)-2-halo-1-phenyl ethanol having the formula [(R)-I]:

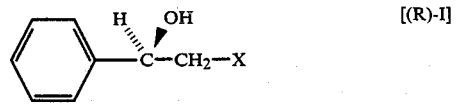

wherein X is a halogen atom, which comprises subjecting a 2-halo-acetophenone having the formula [II]:

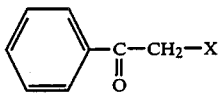

wherein X is as above, to the action of microorganism selected from the group consisting of *Hansenula anomala* IFO 0120, *Hansenula anomala* IFO 0146, *Candida sake* CBS 220, *Candida humicola* CBS 2756, *Candida humicola* CBS 1896, *Rhodotorula glutinis* IFO 1099, *Rhodotorula glutinis var dairensis* IFO 0415, *Torulopsis pinus* IFO 0741, *Hanseniaspora valbyensis* IFO 1758, *Filobasidium capsuligenus* IFO 1119, *Hormoascus platyodis* IFO 1471 and *Koeckera africana* IFO 0869.

4. The process of claim 3, wherein X is Cl or Br in formulas [(R.)-I] and [II].

* * * * *